(12) United States Patent
Chambers

(10) Patent No.: US 7,655,262 B2
(45) Date of Patent: Feb. 2, 2010

(54) HAIR TREATMENT COMPOSITION

(76) Inventor: Warren Chambers, 1445 Burgoyne Rd., Downingtown, PA (US) 19335

( * ) Notice: Subject to any disclaimer, the term of this patent is extended or adjusted under 35 U.S.C. 154(b) by 0 days.

(21) Appl. No.: 11/714,410

(22) Filed: Mar. 6, 2007

(65) Prior Publication Data

US 2008/0219942 A1 Sep. 11, 2008

(51) Int. Cl.
*A61K 36/73* (2006.01)
*A61K 36/02* (2006.01)
*A61K 36/50* (2006.01)

(52) U.S. Cl. .................. 424/765; 424/195.17; 424/583

(58) Field of Classification Search ........................ None
See application file for complete search history.

(56) References Cited

U.S. PATENT DOCUMENTS 4,906,461 A * 3/1990 Chambers .................... 424/74

FOREIGN PATENT DOCUMENTS

DE 2714954 * 10/1978

JP 6071452 A * 9/1994

OTHER PUBLICATIONS

Retrieved from the internet <http://www.onlineconversion.com/density_all.htm>. retrieved on Jan. 2, 2008.*

* cited by examiner

*Primary Examiner*—Patricia Leith
*Assistant Examiner*—Melenie McCormick
(74) *Attorney, Agent, or Firm*—Marvin J. Powell, Esq.; Powell Law Associates, LLC

(57) ABSTRACT

An improved hair treatment composition that strengthens cellulosic fiber found in the composition of hair, that eliminates the degradation of hair, and that provides for skin protection from the adverse reaction of caustic alkaline preparations found in professional hair products that are used in the bleaching and strengthening hair. The composition of the present invention may also be safely used by non professional hair stylist without deteriorating the texture and quality of the end user's hair, without permanent or temporary hair loss, and without injury to the scalp.

1 Claim, No Drawings

HAIR TREATMENT COMPOSITION

FIELD OF INVENTION

The present invention relates to an improved hair treatment composition which strengthens hair and prevents damage, such as hair degradation, temporary or permanent hair loss, as well as provides skin protection from scaring of the scalp that typically results when caustic alkaline preparations are used to chemically treat hair.

More specifically, the improved hair treatment composition of the present invention is useful for preventing damage caused by the use of chemical products, such as bleach, peroxides, sodium hydroxide and ammonium thioglycolate hair treatment preparations that are generally applied to the hair by professional salons or by individuals who choose to purchase hair treatment kits and apply such treatments themselves.

BACKGROUND

The use of chemical treatment processes for hair, such as bleaching, and permanent waving or curling, can adversely affect the texture and condition of hair Furthermore, the use of caustic alkaline ingredient found in most hair care and treatment preparations are causing large numbers of individuals to seek help from dermatologists due to hair loss resulting from chemical treatment. Additionally, adverse affects, such as hair loss and damage to the texture and condition of hair are caused by sewing of synthetic and human hair tracks onto and into natural and real hair fibers.

Hair loss and damage to the texture and condition of the hair are serious problems that continue to exist in the hair care industry. Furthermore, when chemical coloring, bleaching and the use of synthetic hair weaves are utilized by professional salons and non-professionals, the risk of hair loss, and damage to the scalp requiring a physician's care continues to be a serious concern and issues in the hair care industry.

What has been found to be new and unanticipated by the prior art is an improved hair treatment composition which strengthens hair and prevents damage, such as hair degradation, temporary or permanent hair loss, as well as provides skin protection from scaring of the scalp that typically results when caustic alkaline preparations are used to chemically treat hair. An additional benefit of the improved hair treatment composition of the present invention is its usefulness in preventing damage to chemically treated hair caused by the use of chemical products, such as bleach, peroxide, sodium hydroxide and ammonium thioglycolate hair treatment preparations.

SUMMARY OF THE INVENTION

The present invention is directed to an improved hair treatment composition which is effective at strengthening hair fibers which has been damaged by chemical treatment. The hair treatment composition of the present invention comprises a mixture of natural ingredients which may be employed in conjunction with known, wet hair conditioners and after shampoos as well as in conjunction with professional chemical hair treatments. The composition of the present invention includes an aqueous mixture which may be used in conjunction with other hair processing treatments. The composition may be rendered acidic by the addition of apple cider vinegar which allows the composition to be readily employed in conjunction with professional chemical treatments such as bleaching, straightening, and permanent waving. The composition is specifically formulated to prevent breakage and strengthen hair fibers that are damaged by chemical treatments.

The present hair treatment composition is directed and specifically formulated to strengthen the hair and prevent damage to both the hair and irritation to the scalp. Furthermore the improved composition of the present invention is effective at reducing the risk when such caustic preparation are utilized to achieve certain hair styles while simultaneously preserving the health, texture and condition of the user's natural hair.

The improved hair treatment composition of the present invention contains apple cider vinegar, liquid chlorophyll sea kelp, hask placenta, sodium bicarbonate, zeolite, magnesium sulfate, chlorophyll of cactus extract and purified water. The improvement composition will prevent degradation of hair fibers and prevent scalp irritation that could lead to hair loss and maintains the healthy condition and texture of the user's natural hair.

DETAILED DESCRIPTION OF THE INVENTION

The improved hair treatment composition of the present invention is formulated by dissolving a dry phase having magnesium sulfate hepta-hydrate, sodium bicarbonate and zeolite into a wet phase having apple cider vinegar, Icelandic sea kelp chlorophyll extract, cactus chlorophyll, placenta, preservative and de-ionized purified water.

Starting with the dry phase of the composition of the present invention, for every fifty-five gallon batch of the final composition, preferably from about 1.0 pound to about 100 pounds Jumbo Gems™ magnesium sulfate hepta-hydrate fiber strengthener (available from P.Q. Corporation, of Valley Forge, Pa.) are used. Most preferably, the composition includes about 50 pounds of Jumbo Gems magnesium sulfate per fifty-five gallon batch. The addition of the Jumbo Gems magnesium sulfate serves to adjust the pH of the final composition to the desired neutral pH range.

Preferably, from about 1.0 pounds to about 16.0 pounds dry volume ounces of sodium bicarbonate are used in the preparation of a fifty-five gallon batch of the final composition. Most preferably, eight pounds dry volumes of sodium bicarbonate are used.

Preferably, from about 0.5 pounds to about 1.0 pounds dry volume pounds of Zeolite type A, sodium alumino silicate, (hereinafter referred to as "Valfor 100"™ available from P.Q. Corporation, of Valley Forge, Pa. are used in the preparation of a fifty-five gallon batch of the final composition. Most preferably, one-half pound dry volume of Valfor 100 is used.

Moving to the wet dry phase of the composition of the present invention, fifty-five gallon batch of the present composition will preferably comprise from about 1.0 gallons to about 12.0 fluid gallons of cider vinegar, preferably apple cider vinegar. Most preferably, a fifty-five gallon batch has about six gallons of cider vinegar. Typically, cider vinegar would have between four percent and six percent acetic acid. In the present invention, apple cider vinegar having about five percent acetic acid is preferred.

Preferably, at least from 1.0 gallon to about 6.0 gallons of Icelandic sea kelp chlorophyll extract (available from Vege-Kurl Inc, Glendale Calif.) are added to formulate a fifty-five gallon batch of the final composition. Most preferably, 3.0 gallons of wet sea kelp chlorophyll extract are used. The sea kelp is preferably Icelandic sea kelp which has been processed into liquid form. Icelandic sea kelp is generally available. Not intended to be limited by such, it is believed that the addition of the sea kelp chlorophyll imparts beneficial properties to the composition which promote the tensile strength and elasticity of the hair when the composition is used thereon.

Preferably, at least from 1.0 gallon to about 6.0 gallons of chlorophyll of Cactus Extract (hereinafter referred to as Yucca "Filamentosa") available from Nature Inc. Blairstown, Iowa) are used. Most preferably, 3.0 gallons of wet chlorophyll of cactus extract are used.

The composition of the present invention has a placenta extract component. The placenta extract comprises liquid and semi-solid material centrifugally removed from supranatant placenta such as human or bovine placenta. The placenta extract may be added to the present composition as a commercially available placenta extract composition such as the Hask placenta product (hereinafter referred to as "Hask placenta") available from Hask, Inc. of Great Neck, N.Y. A fifty-five gallon batch of the present composition preferably contains between from about 1.0 gallons to about 6.0 gallons of Hask placenta, most preferably 3 fluid gallons. Pure placenta extract may be used in the present compositions in lieu of Hask placenta in amounts equivalent to the placenta component found in the Hask placenta product.

For every fifty-five gallon batch of the final composition, preferably from about 1.0 gallons to about 7.0 gallons of Suttaside A preservative (available from Ruger Chemical of Patterson, New, Jersey) is used, preferably, about 3.5 gallons.

The final component of the wet phase of the composition of the present invention that is required to produce a final batch of about fifty-five gallons is from about 1.0 gallons to about 67 gallons of de-ionized purified water which is readily available in the market, preferably from 34.0 gallons to about 36.5 gallons of de-ionized purified water is needed.

The pH of the present invention compositions is preferably adjusted within the pH range of from about 6.0 to about 7.5. Most preferably, the pH is adjusted to about 7.2. Adjustment of the pH is accomplished by varying the amounts of Jumbo Gems, sodium bicarbonate and vinegar components within the ranges set forth above. Compositions with neutral pH's may be distributed to consumers for use at home.

The present invention also contemplates compositions having a pH of about 4.5 for use by professional hairstyler's in conjunction with acidic hair treatments such as perming. The acidic composition of the present invention may be obtained by the addition of sufficient apple cider vinegar to the above identified neutral compositions to adjust the composition to the desired acid pH. For example, this may be accomplished by adding sufficient volume of apple cider vinegar per fifty-five gallons of the neutral pH compositions.

In use, the compositions of the present invention provide many beneficial advantages. When applied to the hair in combination with other treatments, the compositions decrease damage to the hair from the treatments. When applied separately, the compositions repair hair damage caused by other treatments such as perming and coloring. Application of the compositions prevents chemical burn of the hair, improves the tensile strength and elasticity of the hair, promotes the sheen and softness of the hair, reduces scalp burning and irritation, increases manageability and body of the hair, decreased frizzing of the hair and rejuvenates the hair. The hair treatment compositions are generally compatible with major brands of bleach and perm lotions. When used by professional hairdressers, the compositions also reduce irritation to the hands of the hairdresser associated with the application of other treatments.

The hair treatment compositions of the present invention may be applied to hair either alone or in combination with other chemical treatments. When no other chemical treatments are applied to the hair, it is preferred to spray mist the composition onto the hair until the hair becomes saturated. The treatment is permitted to remain on the hair for a period of time either at ambient temperature (for about 30 or more minutes) or with the addition of heat. Thereafter, the hair is rinsed thoroughly.

When the treatment compositions of the present invention are applied to hair in combination with other chemical treatments such as bleaching, permanent waving, and conditioning treatments, they may be applied before and/or after the application of the other treatments for a period of time as set forth above. The treatment compositions may also be added directly to other chemical treatment compositions such as perm, peroxide, bleach and alkaline solutions.

In order to further illustrate and to explain the present invention, and by no way intending to be limited by such, the following non limiting examples are presented:

EXAMPLE 1

A hair treatment composition is prepared by combining:

| | |
|---|---|
| Zeolite | __ pound |
| Jumbo Gems | 50 pounds |
| Sodium bicarbonate | 8 pounds |
| Apple cider vinegar (5% acetic acid) | 6 gallons |
| Icelandic sea kelp | 3.0 Gallons |
| Hask placenta | 3.0 Gallons |
| Suttaside A | 3.5 Gallons |
| De-ionized water | Remainder |
| TOTAL | 55 Gallons |

A hair treatment composition having a pH of 7.2 is obtained.

EXAMPLE 2

A hair treatment composition is prepared by adding sufficient apple cider vinegar of the composition of Example 1. A hair treatment composition having a pH of 7.2 is obtained.

EXAMPLE 3

In the treatment of damaged or processed hair to obtain permanent waving, a conventional perm solution is reduced by one fluid ounce. One fluid ounce of the hair treatment composition of Example 2 is added to the perm solution and mixed therewith The thusly modified perm composition is applied to hair which is set on perm rods in accordance with the normal application of perm solution. The hair is then rinsed and blotted dry with a towel. Thereafter, the hair is saturated by spraying a mist of the composition of Example 1 on the hair and then blotted with a towel. A conventional neutralizer solution for the perm treatment is then applied. The hair is thoroughly rinsed and the perm rods removed.

EXAMPLE 4

In the treatment of strengthening hair that has been weaken by over processing with alkaline chemicals, braids or extensions, apply magnesium heptahydrate strengthener with any cream conditioner for 30 to 40 minutes, for deep conditioner treatment.

EXAMPLE 5

In the treatment of bleaching hair or lightening hair fibers, apply magnesium heptahydrate strengthener to hair areas that have been lighten for about 10 minutes to 15 minutes.

What is claimed is:

1. A hair treatment composition consisting of:
(a) about 50 pounds of magnesium sulfate,
(b) about 8 pounds of sodium bicarbonate,
(c) about ½ pound of sodium alumina silicate,
(d) about 6 gallons of apple cider vinegar,
(e) about 3 gallons of sea kelp,
(f) about 3 gallons of hask placenta,
(g) about 3.5 gallons of preservative,
(h) about 3 gallons of yucca filamentosa
(i) the remainder of the composition being purified water, wherein the total composition is 55 gallons and wherein said composition has a pH in the range of from about 6.0 to about 7.5.

* * * * *